(12) United States Patent
Muta et al.

(10) Patent No.: US 6,936,268 B1
(45) Date of Patent: Aug. 30, 2005

(54) SHEET-FORM ADHESIVE PREPARATION

(75) Inventors: Kazunori Muta, Saga (JP); Yasuhisa Kose, Saga (JP); Munehiko Hirano, Saga (JP)

(73) Assignee: Hisamitsu Pharmaceutical Co., Inc., Tosu (JP)

( * ) Notice: Subject to any disclaimer, the term of this patent is extended or adjusted under 35 U.S.C. 154(b) by 0 days.

(21) Appl. No.: 09/913,543

(22) PCT Filed: Feb. 18, 2000

(86) PCT No.: PCT/JP00/00931

§ 371 (c)(1),
(2), (4) Date: Aug. 15, 2001

(87) PCT Pub. No.: WO00/48580

PCT Pub. Date: Aug. 24, 2000

(30) Foreign Application Priority Data

Feb. 19, 1999  (JP) ................................ 11-041560

(51) Int. Cl.⁷ ......................... A61K 9/70; A01N 25/34

(52) U.S. Cl. ................. 424/402; 424/400; 424/443

(58) Field of Search ........................... 424/401, 78.02, 424/78.03, 402

(56) References Cited

FOREIGN PATENT DOCUMENTS

| JP | 54-49334 A | | 4/1979 |
|---|---|---|---|
| JP | 57-206614 A | * | 12/1982 |
| JP | 61-260014 A | | 11/1986 |
| JP | 61260014 A | * | 11/1986 |
| JP | 1-46485 B | | 10/1989 |
| JP | 3-16989 B | | 6/1991 |
| JP | 3-188149 A | | 8/1991 |
| JP | 5-295004 A | | 11/1993 |
| JP | 7-25659 B | | 3/1995 |
| JP | 8-53354 A | | 2/1996 |
| JP | 8-291057 A | | 11/1996 |
| JP | 2761936 | | 3/1998 |
| JP | 10-279473 A | | 10/1998 |
| JP | 60-226808 A | | 11/1998 |

* cited by examiner

*Primary Examiner*—Thurman K. Page
*Assistant Examiner*—Sharon Howard
(74) *Attorney, Agent, or Firm*—Wolf, Greenfield & Sacks, P.C.

(57) ABSTRACT

A sheet-form adhesive preparation which gives a comfortable refreshing feeling in use, gives a wet feeling to the skin, and is usable a a cosmetic, medicinal, or quasi-drug preparation for the sake of skin adjustment and beauty. The preparation preferably has a quantity of heat required for water evaporation of 0.6 to 13 (cal) per unit area ($cm^2$) when exposed for 30 minutes to an atmosphere of 25° C. and 60% Rh.

4 Claims, No Drawings

SHEET-FORM ADHESIVE PREPARATION

RELATED APPLICATIONS

This application is a national stage filing under 35 U.S.C. § 371 of PCT application PCT/JP00/00931, filed Feb. 18, 2000. Foreign priority benefits are claimed under 35 U.S.C. §119(a)–(d) or 35 U.S.C. §365(b) of Japan application number 11-41560, filed Feb. 19, 1999.

TECHNICAL FIELD

The present invention relates to a sheet-form adhesive preparation. More particularly, it relates to a sheet-form adhesive preparation that gives a comfortable refreshing feeling in use, gives a wet feeling to the skin, and is usable as a cosmetic, medicinal, or quasi-drug preparation for the sake of skin adjustment and beauty.

BACKGROUND ART

Sheet-form adhesive preparations that are used as tape preparations and wet pack preparations for the treatment of backache, shoulder stiffness, bruising, sprains, etc., wet pack preparations for healing foot tiredness, sheet-form pack preparations for beauty treatments for the face and body, etc. are known. For example, an aqueous adhesive composition that is formed from a polyacrylic acid, a polyacrylate salt, a cellulose derivative, a polyhydric alcohol and a polyvalent metal compound is disclosed in JP, B, 3-16989, a poultice preparation that is formed by using a moisturizing component chosen from sodium hyaluronate, sodium chondroitin sulfate, a lactate salt, a pyrrolidone carboxylic acid, urea, an aloe extract and a *perilla* leaf extract and does not include any medicinal components is disclosed in JP, A, 8-291057, and a foot care sheet preparation for the purpose of eliminating tiredness and swelling of feet, etc. that has an improved effect of introducing a refreshing feeling, etc. due to a component in a hydrated adhesive layer and excellent usability is disclosed in JP, A, 10-279473. In particular, with regard to the pack preparations, a pack preparation that contains as main components a polyacrylate salt, a polyhydric alcohol and water and has excellent water retention and is easily peeled off is disclosed in JP, A, 54-49334, a sheet-form pack preparation that uses a cross-linking type hydrated gel as a base is disclosed in JP, B, 1-46485, a pack preparation to which are added a naturally derived semi-synthetic component as a moisturizing agent and a viscosity-increasing agent is disclosed in JP, A, 5-295004, a sheet-form hydrated pack preparation that is impregnated with alginic acid, polyvinylpyrrolidone and a skin beauty component is disclosed in JP, B, 7-25659, a sheet-form pack preparation that contains xanthan gum, locust bean gum, a water-soluble solvent and water is disclosed in JP, A, 2761936 (JP, A, 3-81213) etc.

However, conventional sheet-form adhesive preparations easily cause a disagreeable feeling such as a pinching feeling or a sore feeling when they are used, and they thus have the problem that they cannot satisfy users' relaxation needs even at the present time when much attention is paid to the boom in sheet cosmetics.

The object of the present invention is therefore to solve the above-mentioned problems of the art and provide a sheet-form adhesive preparation that is safe for the skin, shows excellent effects in cooling the affected area as well as beautifying the skin, and gives an excellent refreshing feeling and user satisfaction when applied and after being peeled off.

DISCLOSURE OF INVENTION

As the present inventors have been carrying out an intensive investigation in order to solve the above-mentioned problems, with regard to a sheet-form adhesive preparation, it has been found that by paying attention to and appropriately adjusting the quantity of heat required for evaporating the water therein, the above-mentioned problems can be solved and a comfortable refreshing feeling in use as well as user satisfaction after peeling off can be greatly improved, and the present invention has thus been accomplished.

That is to say, the present invention relates to a sheet-form adhesive preparation characterized in that the quantity of heat required for the evaporation of water when exposed for 30 minutes to an atmosphere of 25° C. and 60% Rh is 0.6 to 13 (cal) per unit area ($cm^2$).

Furthermore, the present invention relates to the above-mentioned sheet-form adhesive preparation characterized in that it contains 1 to 50 wt % of a glycol and/or a polyhydric alcohol.

Furthermore, the present invention relates to the above-mentioned sheet-form adhesive preparation characterized in that the glycol has a polyether structure and is a polyethylene glycol having an average molecular weight of 200 to 600 and/or a polypropylene glycol having an average molecular weight of 500 to 3000.

Furthermore, the present invention relates to the above-mentioned sheet-form adhesive preparation characterized in that the polyhydric alcohol is a low molecular weight polyhydric alcohol having 2 to 3 hydroxyl groups in its molecular structure.

Furthermore, the present invention relates to the above-mentioned sheet-form adhesive preparation, wherein it is used as a sheet-form pack preparation.

EMBODIMENTS OF THE INVENTION

Modes for carrying out the sheet-form adhesive preparation related to the present invention are explained in detail below.

The quantity of heat required for the evaporation of water referred to in the present invention means that obtained by exposing a support surface to an atmosphere of a temperature of 25±0.5 (° C.) and a humidity of 60±5 (%) for 30 minutes, using the change in weight during that time as the amount of water evaporated from the support surface, calculating the quantity of heat from the latent heat of vaporization at 25° C. and further converting it to a quantity of heat per unit area.

The method of calculation is as follows. Quantity of heat (Cal) required for evaporation of water per unit area ($cm^2$) =Latent heat of vaporization of water at 25° C. (cal/g) ×amount of water evaporated (g)÷sample area ($cm^2$).

The present invention can provide a pack preparation that can give a comfortable refreshing feeling in use as well as greatly improved user satisfaction after peeling off by adjusting the quantity of heat so as to be 0.6 to 13 (cal).

In the present invention, a particularly preferred mode is a sheet-form adhesive preparation requiring a quantity of heat of 4 to 13 (cal). Such a sheet-form adhesive preparation is particularly suitable as a sheet-form pack preparation.

The sheet-form adhesive preparation of the present invention is typically composed of a base containing a moisturizing agent, that is to say, a moisturizing agent, water, a water-soluble polymer, a cross-linking agent and a preservative. Moreover, as necessary, skin beauty components, moisturizing components, antioxidants, tackifiers, solubilizers, colorants, perfumes, surfactants, UV absorbers, inorganic fillers and pH adjusting agents can be added thereto. In the present invention, by appropriately mixing these materials the above-mentioned quantity of heat required for the evaporation of water is adjusted so as to be in a predetermined range.

With regard to the moisturizing agent, a glycol and/or a polyhydric alcohol can be used singly or in combination. The amount of moisturizing agent used relative to the total amount of the base is determined while taking into consideration the tackiness and cohesion of the preparation, degradation in water retention and maintenance of shape before use, non-uniformity of paste gel, degradation in handling, degradation in the user's feeling when it is used, etc., and it is 1 to 50 wt %, preferably 5 to 30 wt %, and more preferably 5 to 25 wt %.

In addition, the glycols in the moisturizing agents can be used as dispersants/solubilizers or plasticizers for the water-soluble polymer, moisturizing components, cross-linking agents, skin beauty components, preservatives, etc. and can also be used to promote the release and diffusion of water. Since the glycols referred to here have a polyether structure and have low hydrophilicity due to the presence of fewer hydroxyl groups than are in the low molecular weight polyhydric alcohols that are commonly used, by utilizing this property the critical relative humidity of the base components excluding water can be lowered, and a larger amount of water can be released to the outside when the product is used. As a result, the skin is moisturized, the heat of vaporization is lost due to water diffusing to the outside, flushing of the face and inflammation can be suppressed while a comfortable refreshing feeling is given. Furthermore, the temperature dependence of the viscosity is low, and when the glycols are mixed with a preparation, maintenance of a stable shape that does not depend on changes in the surroundings can be exhibited. With regard to the glycols having a polyether structure, polyethylene glycol having an average molecular weight of 200 to 600 and polypropylene glycol having an average molecular weight of 500 to 3000 are preferred, and they can be used singly or in combinations of two or more types.

The polyhydric alcohols in the moisturizing agents can be used as dispersants/solubilizers or plasticizers for the water-soluble polymer, moisturizing components, cross-linking agents, skin beauty components, preservatives, etc. and can also suppress the release and diffusion of water. The polyhydric alcohols referred to here are low molecular weight polyhydric alcohols having 2 to 3 hydroxyl groups in their molecular structure, and since they have excellent hydrophilicity, the critical relative humidity of the base components excluding water can be enhanced and the release and diffusion of water in use can be suppressed. With regard to the polyhydric alcohols, propylene glycol, 1,3-butylene glycol and glycerin are preferred, and they can be used singly or in combinations of two or more types.

The balance with which the glycols and/or polyhydric alcohols are mixed with water in the moisturizing agents can give the appropriate moisturization and tackiness to the skin and greatly improve the comfortable refreshing feeling in use as well as the user satisfaction after peeling off.

With regard to the water used in the sheet-form adhesive preparation of the present invention, purified water, sterile water or natural water is used. Water functions as a dispersant/solubilizer for the water-soluble polymer, moisturizing components, cross-linking agents, preservatives, etc. and is particularly important for dispersing/dissolving the glycols and polyhydric alcohols, which form the moisturizing agent, uniformly in the preparation. Moreover, water itself introduces the effects of greatly improving the user's feeling during and after use, moisturizing and giving elasticity by moving into the skin together with a moisturizing component, etc. The amount of water added is therefore determined by taking into consideration the tackiness of the preparation, degradation in water retention before use, degradation in handling, degradation in the user's feeling during use, maintenance of shape before use, etc. and it is added at 30 to 95 wt %, preferably 65 to 90 wt %, and more preferably 70 to 85 wt %. The presence of a large amount of water in the preparation can increase the relative humidity of the preparation itself, it becomes possible to release a larger amount of water to the outside efficiently during use, and as a result the skin can be moisturized, heat of vaporization can be lost by water diffusing to the outside and a comfortable refreshing feeling can be given.

With regard to the water-soluble polymer, gelatin, polyacrylic acid, salts thereof, partially neutralized derivatives thereof, etc. can be cited, and they can be used singly or in combinations of two or more types. With regard to the salts in the polyacrylate salts, metal salts such as the sodium, lithium, potassium, etc. salts are preferred, and those having an average degree of polymerization of 1,000 to 100,000 are suitably used. The amount of water-soluble polymer added is determined by taking into consideration the tackiness and cohesion of the preparation, the maintenance of shape, water absorption ability, non-uniformity of paste, degradation in handling, degradation in the user's feeling during use, viscosity during production, etc., and it is used at 3 to 25 wt %, preferably 5 to 20 wt %, and more preferably 5 to 10 wt %.

With regard to the cross-linking agents, water-insoluble aluminum compounds or polyfunctional epoxy compounds can be used singly or in combinations of two or more types. With regard to the water-insoluble aluminum compounds, aluminum hydroxide, hydrated aluminum silicate, synthetic aluminum silicate, kaolin, aluminum acetate, aluminum lactate, aluminum stearate, etc. can be cited, and they can be used singly or in combinations of two or more types. A water-insoluble aluminum compound, when used, can exhibit an effect of suppressing skin irritation due to its antacid action and a skin astringent action as a result of a trace amount of aluminum ions and, in addition, can introduce a moderate strength to a gel as a filler in terms of the initial physical properties, and can make aluminum ions elute inside the preparation after time has passed so exhibiting the function of compensating for degradation in the gel strength due to decomposition of the polymer over time and breakage of cross-linking covalent bonds between the polymer over time. Furthermore, by adjusting the pH the speed at which the aluminum elutes can be controlled.

With regard to the polyfunctional epoxy compounds, polyethylene glycol diglycidyl ether, ethylene glycol diglycidyl ether, glycerin diglycidyl ether, glycerin triglycidyl ether, propylene glycol diglycidyl ether, polyglycerol polyglycidyl ether, sorbitol polyglycidyl ether, sorbitan polyglycidyl ether, trimethylolpropane polyglycidyl ether, pentaerythritol polyglycidyl ether, resorcinol diglycidyl ether, neopentyl glycol diglycidyl ether, etc. can be cited. These polyfunctional epoxy compounds can be used singly or in combinations of two or more types. The use of a polyfunctional epoxy compound can give excellent water absorption ability and maintenance of shape, and can efficiently form covalent bonds with a water-soluble polymer having a carboxyl group, an amino group, a hydroxyl group, etc. thus enhancing the gel strength. The amount of cross-linking compound added is determined by taking into consideration the cohesion and maintenance of shape of the preparation, degradation in the water absorption ability, degradation over time in the stability of the physical properties of the preparation, degradation in handling, degradation in safety for the skin, degradation in the user's feeling during use, the tackiness, increase in the viscosity during production, non-uniformity of paste due to gelling, etc., and it is used at 0.001 to 20 wt %, preferably 0.005 to 15 wt %, and more preferably 0.01 to 10 wt %.

With regard to the preservatives, p-hydroxybenzoate esters (e.g. methylparaben, ethylparaben, propylparaben), 1,2-pentanediol, benzoic acid, benzoate salts, salicylate salts, sorbic acid, sorbate salts, dehydroacetate salts, 4-isopropyl-3-methylphenol, 2-isopropyl-5-methylphenol, phenol, hinokitiol, cresol, 2,4,4'-trichloro-2'-hydroxydiphenyl ether, 3,4,4'-trichlorocarbamide, chlorobutanol, benzalkonium chloride, benzethonium chloride, etc. can be cited, and they can be used singly or in combinations of two or more types. Among these, p-hydroxybenzoate esters are preferred. With regard to the amount added, it is determined by taking into consideration putrefaction of the preparation due to the occurrence of mold or bacteria during storage, degradation in the user's feeling during and after use, changes in tackiness and cohesion of the preparation, irritation of the user's feeling, an unpleasant feeling due to an antiseptic smell, etc., and it is used at 0.005 to 10 wt %, preferably 0.01 to 5 wt %, and more preferably 0.01 to 1 wt %.

The sheet-form adhesive preparation of the present invention can appropriately contain, in addition to the above-mentioned base components, known medicinal components, skin beauty components, moisturizing components, refrigerants or coolants, antioxidants, tackifiers, solubilizers, colorants, perfumes, surfactants, UV absorbing agents, inorganic fillers, pH adjusting agents, etc. in appropriate amounts according to the purpose for which the adhesive preparation as described above will be used.

With regard to the medicinal components, there are no particular restrictions as long as they are drugs capable of percutaneous absorption, for example, steroidal anti-inflammatory drugs such as prednisolone, dexamethasone, hydrocortisone, fluocinolone acetonide, betamethasone valerate, betamethasone dipropionate, clobetasone butyrate and prednisolone succinate, nonsteroidal antiinflammatory agents, ester derivatives thereof and salts thereof such as methyl salicylate, glycol salicylate, indomethacin, ketoprofen, diclofenac, ibuprofen, flurbiprofen, felbinac, ketorolac, loxoprofen, suprofen, pranoprofen, tiaprofen, flufenamic acid, aspirin, actarit, mizoribine, oxaprozin, mofezolac, etodolac, auranofin and indomethacin farnesil, antiallergic drugs such as tranilast, azelastine, ketotifen, ibudilast, oxatomide, emedastin and epinastin, antihistamine drugs such as diphenhydramine, chlorpheniramine, promethazine and tripelennamine, drugs acting on the central nervous system such as chlorpromazine, nitrazepam, diazepam, phenobarbital and reserpine, hormonal drugs such as insulin, testosterone, norethisterone, methyltestosterone, progesterone and estradiol, antihypertensive drugs such as clonidine, reserpine, guanethidine sulfate, efonidipine, alprenolol and nifedipine, cardiac stimulants such as digitoxin and digoxin, antiarrhythmic drugs such as propranolol hydrochloride, procainamide hydrochloride, ajmaline, pindolol and tulobuterol hydrochloride, coronary vasodilators such as nitroglycerin, isosorbide nitrate, papaverine hydrochloride, nifedipine, diltiazem and nicorandil, local anesthetics such as lidocaine, procaine, procaine hydrochloride, benzocaine and tetracaine, painkillers such as morphine, fentanyl or salts thereof, aspirin, codeine, acetanilide and aminopyrine, muscle relaxants such as tizanidine, eperisone, tolperisone, inaperisone and dantrolene, antifungal drugs such as acetophenylamine, nitrofurazone, pentamycin, naphthiomate, miconazole, omoconazole, clotrimazole and butenafine hydrochloride, antineoplastic drugs such as 5-fluorouracil, busulfan, actinomycin, bleomycin and mitomycin, urinary incontinence drugs such as terolidine hydrochloride and oxybutynin hydrochloride, antiepileptic drugs such as nitrazepam and meprobamate, anti parkinsonism drugs such as chlorzoxazone, levodopa, amantadine, selegiline hydrochloride, ranolazine hydrochloride and ropinirole hydrochloride, antiemetic drugs such as granisetron, azasetron, ondansetron and ramosetron, drugs for the treatment of frequent urination such as oxybutynin, Ca antagonists such as nifedipine, psychotropic drugs such as imipramine, drugs for the treatment of vertigo such as difenidol and betahistine, cardiovascular drugs such as benzothiazepine, antitussive drugs such as ketotifen, tulobuterol and tranilast, cerebral circulation activators such as vinpocetine, nicergoline, nicorandil, clentiazem maleate, fasudil hydrochloride, benidipine hydrochloride and efonodipine hydrochloride, drugs for combating multiinfarct dementia such as docosahexaenoic acid, vinconate hydrochloride and nebracetam fumarate, drugs for the treatment of Alzheimer's disease such as donepezil hydrochloride, amiridine hydrochloride and memantine hydrochloride, polypeptide system hormonal drugs such as lutenizing hormone-releasing hormone and thyrotropin releasing hormone, immunomodulators such as polysaccharides, auranofin and lobenzarit, choleretic drugs such as ursodeoxycholic acid, diuretic drugs such as hydroflumethiazide, diabetic drugs such as tolbutamide, drugs for the treatment of gout such as colchicine, drugs to assist in stopping smoking such as nicotine and, furthermore, drugs such as vitamins, prostaglandins, stimulant drugs, sleeping sedative drugs, autonomic nervous system drugs and telangiectatic drugs can be cited.

With regard to the skin beauty components, water-soluble placenta extract, allantoin, lecithin, amino acids, kojic acid, proteins, saccharides, hormones, placenta extract, components extracted from various types of herbal medicine such as aloe, sponge gourd and liquorice, vitamin A, vitamin C, vitamin D, vitamin E and other vitamins, etc. can be cited. Also, drugs having a skin whitening action such as diphenhydramine hydrochloride, diphenhydramine salicylate, diphenhydramine tannate, triprolidine hydrochloride, mequitazine, chlorpheniramine maleate, chlorpheniramine d-maleate, clemastine fumarate, promethazine hydrochloride, tranilast, sodium cromoglycate, ketotifen, arylsulfatase B, bufexamac, bendazac, butyl flufenamate, ibuprofen, indomethacin, aspirin, flurbiprofen, ketoprofen, piroxicam and ibuprofen piconol, 5,6-dehydroarachidonic acid, 5,6-methano-LTA$_4$, esculetin, eupatilin, 4-demethyleupatilin, caffeinic acid and benoxaprofen can be cited.

With regard to the moisturizing components, an aqueous solution of succinylkefiran, an aqueous solution of acetylkefiran, an aqueous solution of maleylkefiran, malt sprout extract, Rosae fructus extract, orange extract, orange fruit juice, raspberry extract, kiwi extract, cucumber extract, gardenia extract, grapefruit extract, *Crataegus cuneata* extract, xanthoxylum extract, *Crataegus oxycantha* extract, *Juniperus communis* extract, Zizyphi fructus extract, *Ziziphus jujuba* extract, duke extract, tomato extract, grape extract, sponge gourd extract, lime fruit juice, apple extract, apple fruit juice, lemon extract, lemon fruit juice, etc. can be added singly or in combinations of two or more types. Moreover, fruit extract (fruit juices) also function as perfumes.

With regard to the refrigerants or coolants, L-menthol, dL-menthol, dL-camphor, eucalyptus oil, peppermint oil, isopulegol, 3-L-menthoxypropane-1,2-diol, menthylpyrrolidonecarboxylate, L-menthyl-3-hydroxybutyrate, etc. can be added as required.

With regard to the antioxidants, ascorbic acid, propyl gallate, butyl hydroxyanisole, dibutyl hydroxytoluene, nordihydroguaiaretic acid, tocopherol, tocopherol acetate, etc. can be added.

With regard to the tackifiers, casein, pullulan, agar, dextran, sodium alginate, soluble starch, carboxy starch, dextrin, carboxymethyl cellulose, sodium carboxymethyl cellulose, methyl cellulose, ethyl cellulose, hydroxyethyl cellulose, polyvinyl alcohol, polyethylene oxide, polyacrylamide, polyacrylic acid, polyvinylpyrrolidone, carboxyvinyl polymer, polyvinyl ether, methyl vinyl ether-maleic anhydride copolymer, isobutylene-maleic anhydride copolymer, polyethyleneimine, etc. can be added.

With regard to the solubilizers, benzyl alcohol, pyrrothiodecane, peppermint oil, isopropyl myristate, crotamiton, etc. can be added.

With regard to the colorants, those that can have a large influence on the image of the preparation and contribute to an improvement in the user's feeling during use and a feeling of skin revitalization are preferred, for example, approved colorants such as Red No. 2 (amaranth), Red No. 3 (erythrosine), Red No. 102 (new coccine), Red No. 104 (1) (phloxine B), Red No. 105 (1) (rose bengal), Red No. 106 (acid red), Yellow No. 4 (tartrazine), Yellow No. 5 (sunset yellow FCF), Green No. 3 (fast green FCF), Blue No. 1 (brilliant blue FCF) and Blue No. 2 (*indigo* carmine) can be cited, but they are not particularly limited thereby.

With regard to the surfactants, anionic surfactants such as sodium dioctylsulfosuccinate, alkylsulfate salts, 2-ethylhexylalkylsulfate ester sodium salt and sodium n-dodecylbenzenesulfonate, cationic surfactants such as hexadecyltrimethylammonium chloride, octadecyldimethylbenzylammonium chloride and polyoxyethylenedodecylmonomethylammonium chloride, nonionic surfactants such as polyoxyethylene stearyl ether, polyoxyethylene tridecyl ether, polyoxyethylene nonyl phenyl ether, polyoxyethylene octyl phenyl ether, polyoxyethylene monostearate, sorbitan monostearate, sorbitan monopalmitate, sorbitan sesquioleate, polyoxyethylene sorbitan monolaurate, polyoxyethylene sorbitan monooleate, glycerol monostearate, polyglycerol fatty acid esters and polyoxyethylene octadecylamine can be added.

With regard to the UV absorbers, p-aminobenzoic acid, p-aminobenzoate esters, amyl p-dimethylaminobenzoate, salicylate esters, menthyl anthranilate, umbelliferone, esculin, benzyl cinnamate, cinoxate, guaiazulene, urocanic acid, 2-(2-hydroxy-5-methylpheny)benzotriazole, 4-methoxybenzophenone, 2-hydroxy-4-methoxybenzophenone, dioxybenzone, octabenzone, dihydroxydimethoxybenzophenone, sulisobenzone, benzoresorcinol, octyldimethyl p-aminobenzoate, ethylhexyl p-methoxy cinnamate, etc. can be added.

With regard to the inorganic fillers, titanium oxide, talc, zinc oxide, hydrated silica, magnesium carbonate, calcium hydrogenphosphate, magnesium silicate, diatomaceous earth, silicic anhydride, bentonite, etc. can be added.

With regard to the pH adjusting agents, acetic acid, formic acid, lactic acid, tartaric acid, oxalic acid, benzoic acid, glycolic acid, malic acid, citric acid, hydrochloric acid, nitric acid, sulfuric acid, sodium hydroxide, potassium hydroxide, methylamine, ethylamine, propylamine, dimethylamine, diethylamine, dipropylamine, trimethylamine, triethylamine, tripropylamine, monomethanolamine, monoethanolamine, monopropanolamine, dimethanolamine, diethanolamine, dipropanolamine, trimethanolamine, triethanolamine, tripropanolamine, etc., can be added.

It is desirable to give proper consideration to the pH of a paste to which each of the above-mentioned components has been added appropriately in an appropriate amount so that the skin will not be irritated, and its pH is in the range of 4 to 8, preferably 5.5 to 7.5, and more preferably 6 to 7.

Furthermore, with regard to supports on which the paste is coated, those having flexibility such as breathable or vapor-permeable synthetic resin films such as polyethylene, polypropylene, polyethylene terephthalate, ethylene-vinyl acetate copolymer, vinyl chloride, polyurethane, polyester, polyamide and rayon, non-woven stretch fabrics, non-woven paper, laminates of the above-mentioned synthetic resin films or sheets and non-woven fabric or non-woven paper, non-woven fabrics such as absorbent cotton, fabrics, stretch fabric, paper and cellophane can be cited, and they can be chosen appropriately according to the purpose of the application. Moreover, by coating a paste on a base fabric made of a flexible support and covering the surface of the paste layer with a peelable film or paper the stability of the preparation can be maintained. With regard to the peelable film or paper, a separation line or perforation, etc. is provided for easy use and it can thus be formed into a shape that is easily peeled off and attached. The color of the base fabric is not particularly restricted but it can have a large influence on the image of the preparation and contribute to an improvement in the user's feeling during use and a feeling of skin revitalization; white, skin color, yellow, red, orange, green, blue, pink, light blue, brown, etc. can be cited and the shade is preferably adjusted as necessary.

With regard to a process for producing the sheet-form adhesive preparation of the present invention, preparation of a sheet-form pack preparation is described as a representative example. With regard to a process for the production of a sheet-form pack preparation, the above-mentioned components are uniformly mixed and/or dissolved in a mixer, the mixture is spread on an undyed or dyed base fabric, a peelable paper is attached thereto and it is cut into the shape of a face. Eye, nose, mouth and chin parts are cut into appropriate shapes so as to be easily handled. For the purpose of application to parts of the face, they can be shaped so that they can be properly applied to an intended part, for example, as a nose pack for applying to the nose or an eye pack for applying to the area around the eyes. In addition, the sheet-form pack preparation is desirably stored in a hermetic bag or container until it is used in terms of preventing degradation of the effects due to contamination and evaporation of volatile materials during storage, etc.

With regard to the sheet-form adhesive preparation of the invention of the present application, the quantity of heat required for water evaporation when exposed for 30 minutes to an atmosphere of 25° C. and 60% Rh is 0.6 to 13 (cal) per unit area ($cm^2$).

EXAMPLES

The sheet-form adhesive preparation of the present invention is explained further in detail below by reference to Examples and Test Examples, but the present invention is in no way limited thereby.

Example 1

4 wt % of synthetic aluminum silicate was dispersed in 78.4 wt % of purified water, 1 wt % of gelatin, 0.05 wt % of sorbitol polyglycidyl ether, 0.2 wt % of a water-soluble placenta extract, 0.1 wt % of allantoin and 0.25 wt % of methylparaben were added to and dissolved in the above, and a mixture of 6 wt % of sodium polyacrylate and 10 wt % of polyethylene glycol was further added thereto and stirred until the mixture became uniform. The mixture was then spread at a thickness of about 1.4 mm on a base fabric and a film was attached thereto. After the attachment it was cut into the shape of a face and the eye, nose, mouth and chin parts were cut into appropriate shapes to give a sheet-form pack preparation.

Example 2

0.7 wt % of kaolin was dispersed in 95 wt % of purified water, 3 wt % of gelatin, 0.05 wt % of polyethylene glycol diglycidyl ether and 0.25 wt % of methylparaben were added to and dissolved in the above, and 1 wt % of polypropylene glycol was further added thereto and stirred until the mixture became uniform. The mixture was then poured into a mold at a thickness of about 2 mm on a base fabric and cooled and shaped, and a film was attached thereto. After the attachment it was cut into the shape of a face and the eye, nose, mouth and chin parts were cut into appropriate shapes to give a sheet-form pack preparation.

Example 3

5 wt % of kaolin and 1 wt % of aluminum acetate were dispersed in 71.19 wt % of purified water, 0.5 wt % of gelatin, 0.045 wt % of a grapefruit extract, 0.045 wt % of an apple extract, 0.003 wt % of orange fruit juice, 0.002 wt % of lemon fruit juice, 0.005 wt % of lime fruit juice and 0.1 wt % of methylparaben were added to and dissolved in the above, and a mixture of 7 wt % of sodium polyacrylate, 5 wt % of polyethylene glycol, 5 wt % of polypropylene glycol, 1 wt % of propylene glycol, 4 wt % of 1,3-butylene glycol, 0.1 wt % of ethylparaben and 0.01 wt % of propylparaben was further added thereto and stirred until the mixture became uniform. The mixture was then spread at a thickness of about 1.4 mm on a base fabric and a film was attached thereto. After the attachment it was cut into the shape of a face and the eye, nose, mouth and chin parts were cut into appropriate shapes to give a sheet-form pack preparation.

Example 4

1 wt % of gelatin, 0.08 wt % of polyglycerol polyglycidyl ether and 0.1 wt % of a 2% aqueous solution of succinylkefiran were added to and dissolved in 60 wt % of purified water, and a mixture of 3.8 wt % of sodium polyacrylate, 0.02 wt % of propylparaben and 35 wt % of glycerin was added thereto and stirred until the mixture became uniform. The mixture was then spread at a thickness of about 1 mm on a base fabric and a film was attached thereto. After the attachment it was cut into the shape of a face and the eye, nose, mouth and chin parts were cut into appropriate shapes to give a sheet-form pack preparation.

Example 5

2 wt % of synthetic aluminum silicate and 0.7 wt % of aluminum acetate were dispersed in 60 wt % of purified water, 1 wt % of gelatin, 0.1 wt % of glycerin triglycidyl ether and 0.1 wt % of methylparaben were added to and dissolved in the above, and a mixture of 6 wt % of sodium polyacrylate, 0.1 wt % of ethylparaben and 30 wt % of polyethylene glycol was further added thereto and stirred until the mixture became uniform. The mixture was then spread at a thickness of about 1.4 mm on a base fabric and a film was attached thereto. After the attachment it was cut into the shape of a face and the eye, nose, mouth and chin parts were cut into appropriate shapes to give a sheet-form pack preparation.

Example 6

0.5 wt % of synthetic aluminum silicate and 1 wt % of kaolin were dispersed in 34.7 wt % of purified water, 2 wt % of gelatin, 0.05 wt % of sorbitol polyglycidyl ether and 0.25 wt % of methylparaben were added to and dissolved in the above, a mixture of 4 wt % of polyacrylic acid, 3.5 wt % of sodium polyacrylate, 3.5 wt % of polyvinylpyrrolidone and 50 wt % of glycerin was further added thereto, and a solution of 0.2 wt % of ketoprofen dissolved in 0.3 wt % of crotamiton was added thereto and stirred until the mixture became uniform. The mixture was then spread at a thickness of about 0.5 mm on a base fabric and a film was attached thereto. After the attachment it was cut into a 10 cm×14 cm shape to give a sheet-form pack preparation.

Example 7

5 wt % of kaolin was dispersed in 49.7 wt % of purified water, 2 wt % of gelatin and 0.5 wt % of methylparaben were added to and dissolved in the above, a mixture of 2 wt % of polyacrylic acid, 0.5 wt % of sodium carboxymethyl cellulose, 3.5 wt % of sodium polyacrylate, 1 wt % of polyvinylpyrrolidone and 35 wt % of glycerin was added thereto, and a mixed solution of 0.5 wt % of glycol salicylate and 0.3 wt % of tocopherol acetate was further added and stirred until the mixture became uniform. The mixture was then spread at a thickness of about 1 mm on a base fabric and a film was attached thereto. After the attachment it was cut into a 10 cm×14 cm shape to give a sheet-form pack preparation.

COMPARATIVE EXAMPLE

A comparison was made with the Examples in the Test Examples below.

Comparative Example 1

0.5 wt % of synthetic aluminum silicate and 5 wt % of kaolin were dispersed in 26 wt % of purified water, 2 wt % of gelatin, 0.05 wt % of sorbitol polyglycidyl ether, 0.2 wt % of a 2% aqueous solution of succinylkefiran and 0.25 wt % of methylparaben were added to and dissolved in the above, and a mixture of 4 wt % of polyacrylic acid, 3.5 wt % of sodium polyacrylate, 3.5 wt % of polyvinylpyrrolidone and 55 wt % of glycerin was further added thereto and stirred until the mixture became uniform. The mixture was then spread at a thickness of about 0.5 mm on a base fabric and a film was attached thereto. After the attachment it was cut into the shape of a face and the mouth and chin parts were cut into appropriate shapes to give a sheet-form pack preparation.

Comparative Example 2

2.5 wt % of agar, 0.2 wt % of a water-soluble placenta extract, 0.1 wt % of allantoin and 0.2 wt % of methylparaben were added to and dissolved in 97 wt % of purified water. This was then poured into a mold at a thickness of about 2 mm on a base fabric and cooled and shaped, and a film was attached thereto. After the attachment it was cut into the shape of a face and the eye, nose, mouth and chin parts were cut into appropriate shapes to give a sheet-form pack preparation.

Test Example 1

Measurement of Quantity of Heat Required for Evaporation of Water per Unit Area

The quantity of heat required for evaporation of water per unit area when exposed for 30 minutes to an atmosphere of 25° C. and 60% Rh was measured for Examples 1, 2, 3, 4, 5, 6 and 7 and Comparative Examples 1 and 2, and the results are given in Table 1. The test was carried out by exposing the support surface of a sample that had been cut into a 3 cm×3 cm shape to an atmosphere at a temperature of 25±0.5 (° C.) and a humidity of 60±5 (%) for 30 minutes, using the change in weight during that time as the amount of water evaporated from the support surface, calculating the quantity of heat from the latent heat of vaporization at 25° C. and further converting it to the quantity of heat per unit area.

TABLE 1

|  | Quantity of heat (cal) |
|---|---|
| Example 1 | 11.5 |
| Example 2 | 13.0 |
| Example 3 | 10.8 |
| Example 4 | 4.9 |
| Example 5 | 9.8 |
| Example 6 | 0.6 |
| Example 7 | 2.3 |
| Comparative Example 1 | 0.3 |
| Comparative Example 2 | 13.7 |

Test Example 2

Test for the Evaluation of User's Feeling

A test of the user's feeling was carried out for Examples 1, 2 and 4 and Comparative Examples 1 and 2. The test was carried out by giving one of each of the samples to 40 females in their twenties who applied one to the face each day. The testees subsequently provided an evaluation using 5 grades in terms of 'comfortable feeling in use (refreshing feeling)' and 'user satisfaction after peeling off'. Table 2 shows the test results for 'comfortable feeling in use (refreshing feeling)' and Table 3 shows the results for 'user satisfaction after peeling off'.

TABLE 2

'Comfortable feeling in use (refreshing feeling)'

(Number of people)

|  | Very good | Good | Fair | Poor | Very poor |
|---|---|---|---|---|---|
| Example 1 | 20 | 18 | 2 | 0 | 0 |
| Example 2 | 16 | 18 | 4 | 2 | 0 |
| Example 4 | 7 | 23 | 6 | 4 | 0 |
| Comparative Example 1 | 0 | 6 | 10 | 13 | 11 |
| Comparative Example 2 | 1 | 5 | 24 | 6 | 4 |

TABLE 3

'User satisfaction after peeling off'

(Number of people)

|  | Very good | Good | Fair | Poor | Very poor |
|---|---|---|---|---|---|
| Example 1 | 6 | 27 | 4 | 3 | 0 |
| Example 2 | 8 | 24 | 4 | 4 | 0 |
| Example 4 | 2 | 25 | 9 | 4 | 0 |
| Comparative Example 1 | 0 | 4 | 19 | 12 | 5 |
| Comparative Example 2 | 0 | 16 | 23 | 1 | 0 |

From the above, it was found that the sheet-form adhesive preparation of the present invention has excellent user satisfaction in use and after peeling off. It was also found that it has an excellent effect on the skin and an excellent relaxing effect.

INDUSTRIAL APPLICABILITY

With regard to the sheet-form adhesive preparation of the present invention, since the quantity of heat required for the evaporation of water is adjusted to a predetermined level, not only is there a refreshing feeling in use but also the user satisfaction after peeling off is greatly improved. Since the sheet-form adhesive preparation of the present invention is excellent in terms of safety for the skin, refreshing feeling, the user's feeling and effect on the skin, it can be applied in the fields of medicinal and quasi-drug preparations and cosmetic products for skin adjustment and beauty and is industrially very useful.

What is claimed is:

1. A sheet-form adhesive preparation characterized in that the quantity of heat required for the evaporation of water when exposed for 30 minutes to an atmosphere of 25° C. and 60% Rh is 0.6 to 13 (cal) per unit area ($cm^2$), and in that it contains 1 to 30 wt % of a glycol, wherein the glycol has a polyether structure and is a polyethylene glycol having an average molecular weight of 200 to 600 and/or a polypropylene glycol having an average molecular weight of 500 to 3000, further comprising one or more water-soluble polymers selected from the group consisting of gelatin, polyacrylic acid, salts thereof, and partially neutralized derivatives thereof.

2. The sheet-form adhesive preparation according to claim 1 in which it is used as a sheet-form pack preparation.

3. The sheet-form adhesive preparation according to claim 1, further comprising a polyhydric alcohol.

4. The sheet-form adhesive preparation according to claim 3 characterized in that the polyhydric alcohol is a low molecular weight polyhydric alcohol having 2 to 3 hydroxyl groups in its molecular structure.

* * * * *

(12) INTER PARTES REEXAMINATION CERTIFICATE (478th)
United States Patent
Muta et al.

(10) Number: US 6,936,268 C1
(45) Certificate Issued: Oct. 22, 2012

(54) SHEET-FORM ADHESIVE PREPARATION

(75) Inventors: Kazunori Muta, Saga (JP); Yasuhisa Kose, Saga (JP); Munehiko Hirano, Saga (JP)

(73) Assignee: Hisamitsu Pharmaceutical Co., Inc., Tashirodaikanmachi, Tosu-shi, Saga (JP)

Reexamination Request:
No. 95/001,591, Mar. 31, 2011

Reexamination Certificate for:
Patent No.: 6,936,268
Issued: Aug. 30, 2005
Appl. No.: 09/913,543
Filed: Aug. 15, 2001

(21) Appl. No.: 95/001,591

(22) PCT Filed: Feb. 18, 2000

(86) PCT No.: PCT/JP00/00931
§ 371 (c)(1),
(2), (4) Date: Aug. 15, 2001

(87) PCT Pub. No.: WO00/48580
PCT Pub. Date: Aug. 24, 2000

(30) Foreign Application Priority Data

Feb. 19, 1999 (JP) .................................... 11-041560

(51) Int. Cl.
| | |
|---|---|
| *A61K 8/02* | (2006.01) |
| *A61K 9/70* | (2006.01) |
| *A61K 47/10* | (2006.01) |
| *A61K 47/30* | (2006.01) |
| *A61L 15/44* | (2006.01) |
| *A61Q 19/00* | (2006.01) |
| *A61Q 19/10* | (2006.01) |

(52) U.S. Cl. ..................... 424/402; 424/400; 424/443
(58) Field of Classification Search .................... None
See application file for complete search history.

(56) References Cited

To view the complete listing of prior art documents cited during the proceeding for Reexamination Control Number 95/001,591, please refer to the USPTO's public Patent Application Information Retrieval (PAIR) system under the Display References tab.

*Primary Examiner* — Gary Kunz

(57) ABSTRACT

A sheet-form adhesive preparation which gives a comfortable refreshing feeling in use, gives a wet feeling to the skin, and is usable a a cosmetic, medicinal, or quasi-drug preparation for the sake of skin adjustment and beauty. The preparation preferably has a quantity of heat required for water evaporation of 0.6 to 13 (cal) per unit area ($cm^2$) when exposed for 30 minutes to an atmosphere of 25° C. and 60% Rh.

INTER PARTES REEXAMINATION CERTIFICATE ISSUED UNDER 35 U.S.C. 316

THE PATENT IS HEREBY AMENDED AS INDICATED BELOW.

AS A RESULT OF REEXAMINATION, IT HAS BEEN DETERMINED THAT:

Claims 1-4 are cancelled.

\* \* \* \* \*